United States Patent
Shimuta

(10) Patent No.: US 10,470,715 B2
(45) Date of Patent: Nov. 12, 2019

(54) MOBILE DEVICE

(71) Applicant: MURATA MANUFACTURING CO., LTD., Nagaokakyo-Shi, Kyoto-fu (JP)

(72) Inventor: Toru Shimuta, Nagaokakyo (JP)

(73) Assignee: MURATA MANUFACTURING CO., LTD., Nagaokakyo-Shi, Kyoto-Fu (JP)

(*) Notice: Subject to any disclaimer, the term of this patent is extended or adjusted under 35 U.S.C. 154(b) by 1378 days.

(21) Appl. No.: 14/246,715

(22) Filed: Apr. 7, 2014

(65) Prior Publication Data
US 2014/0249763 A1 Sep. 4, 2014

Related U.S. Application Data

(63) Continuation of application No. PCT/JP2012/006019, filed on Sep. 21, 2012.

(30) Foreign Application Priority Data

Oct. 11, 2011 (JP) .................................. 2011-223951

(51) Int. Cl.
| A61B 5/00 | (2006.01) |
| A61B 5/0245 | (2006.01) |
| A61B 5/0404 | (2006.01) |

(52) U.S. Cl.
CPC .......... *A61B 5/7207* (2013.01); *A61B 5/0245* (2013.01); *A61B 5/0404* (2013.01); *A61B 5/6898* (2013.01)

(58) Field of Classification Search
CPC .... G06Q 10/00; A61B 5/7207; A61B 5/0245; A61B 5/0404; A61B 5/6898; A61B 5/00

USPC ............. 702/19, 21, 22, 85, 104, 116; 705/2
See application file for complete search history.

(56) References Cited

U.S. PATENT DOCUMENTS

| 5,735,799 A | 4/1998 | Baba et al. |
| 8,303,512 B2 | 11/2012 | Kosuda et al. |
| 8,437,824 B2* | 5/2013 | Moon ................... A61B 5/0245 600/323 |
| 2008/0004904 A1* | 1/2008 | Tran ...................... A61B 5/0006 705/2 |
| 2008/0214903 A1 | 9/2008 | Orbach |
| 2010/0289772 A1* | 11/2010 | Miller ................... G06F 3/0421 345/175 |

FOREIGN PATENT DOCUMENTS

| CN | 201355840 Y | 12/2009 |
| CN | 201504263 U | 6/2010 |
| JP | 2000051164 A | 2/2000 |
| JP | 3303299 B2 | 7/2002 |
| JP | 2003-047600 A | 2/2003 |
| JP | 3459463 B2 | 10/2003 |

(Continued)

OTHER PUBLICATIONS

Written Opinion and International Search Report issued in PCT/JP2012/006019 dated Oct. 30, 2012.

*Primary Examiner* — Mohamed Charioui
*Assistant Examiner* — Catherine T. Rastovski
(74) *Attorney, Agent, or Firm* — Arent Fox LLP

(57) ABSTRACT

A mobile device including a biosensor for obtaining biological signals in which biological information can be obtained stably while the mobile device is being held with a hand and is used, without providing a sensor specially used for detecting body motion generated by operating the mobile device.

19 Claims, 11 Drawing Sheets

(56) References Cited

FOREIGN PATENT DOCUMENTS

| | | | |
|---|---|---|---|
| JP | 2004-298609 A | | 10/2004 |
| JP | 2004298609 A | * | 10/2004 |
| JP | 2004-348382 A | | 12/2004 |
| JP | 3726832 B2 | | 12/2005 |
| JP | 3767449 B2 | | 4/2006 |
| JP | 2008-229092 A | | 10/2008 |
| JP | 2010-220807 A | | 10/2010 |
| WO | WO 99/32030 A1 | | 7/1999 |
| WO | WO 2011/040877 A1 | | 4/2011 |

* cited by examiner

MOBILE DEVICE

The present application is a continuation of PCT/JP2012/006019 filed Sep. 21, 2012, which claims priority to Japanese Patent Application No. 2011-223951, filed Oct. 11, 2011, the entire contents of each of which are incorporated herein by reference.

FIELD OF THE INVENTION

The present invention relates to a mobile device, in particular, to a mobile device including a biosensor for obtaining biological information.

BACKGROUND OF THE INVENTION

These days, people are more and more concerned about health maintenance and promotion. Accordingly, it is desirable for health care that people can more handily obtain biological information, such as the pulse and electrocardiograms, in everyday life. In order to satisfy such a demand, for example, cellular phones including a biosensor, are being developed. By including a biosensor in a mobile device which is operated while being held with a hand, such as a cellular phone, a user is able to obtain biological information while using a regular function of the device. That is, while holding a cellular phone and performing an operation, such as inputting/selecting of a telephone number or writing email, the user is able to obtain biological information concerning the user.

However, even if a biosensor is disposed in an area where a hand contacts while a user is operating a mobile device, such as a cellular phone, parts of the user's body other than a finger used for performing an operation may move together with this finger. This may cause noise and may be contained in an output from the biosensor. In order to address such a problem, a technology for detecting body motion of a subject and removing noise produced by such body motion from a biological signal is known. Patent Document 1 discloses a pulse monitor including an acceleration sensor. This pulse monitor is worn by a subject's wrist and monitors a change in the absorbance of a subject part, so that it can calculate the pulse while the subject is walking or running. In this case, in the pulse monitor, the acceleration of an arm is detected by using the acceleration sensor, and noise produced by the motion of the arm is removed on the basis of detection results.

Patent Document 2 discloses a blood glucose meter including a pressure sensor. This glucose meter measures the absorbance of a subject part so as to calculate the blood glucose level. In this case, in this blood glucose meter, contact pressure of a subject part is detected by using the pressure sensor. If a significant change in the contact pressure due to the movement of the subject part is observed, obtained measurement data is discarded.

Patent Document 1: Japanese Patent No. 3726832
Patent Document 2: Japanese Patent No. 3767449

In order to detect and remove motion body noise, an acceleration sensor may be mounted on a mobile device, such as the pulse monitor disclosed in Patent Document 1. However, the acceleration of a mobile device and the motion (acceleration) of a hand (finger) do not necessary coincide with each other. More specifically, if a mobile device is held with a hand and is operated with a finger, a user may operate the mobile device almost without moving the mobile device but only by moving a finger. In this case, it is difficult to detect and remove motion body noise by using an acceleration sensor.

Alternatively, in order to detect and remove body motion noise, a pressure sensor may be used. However, when an electrocardiogram sensor or a temperature sensor is used as a biosensor, even if contact pressure is changed, a high level of noise is unlikely to occur, which may lead to incorrect detection. Additionally, the provision of an acceleration sensor, a pressure sensor, or a sensor specially used for detecting body motion unfavorably increases the cost of a mobile device.

SUMMARY OF THE INVENTION

The present invention has been made in order to solve the above-described problems. It is an object of the present invention to provide a mobile device including a biosensor for obtaining biological signals, in which biological information can be obtained stably while the mobile device is being held with a hand and is used, without providing a sensor specially used for detecting body motion generated by operating the mobile device.

A mobile device according to the present invention is a mobile device which is held with a hand and is operated. The mobile device includes: a biosensor for obtaining a biological signal from a hand holding the mobile device; operation means for detecting an operation performed by using a hand; specifying means for specifying a timing of an operation detected by the operation means; noise occurrence determining means for making a noise occurrence determination whether or not a peak of a biological signal obtained by the biosensor is body motion noise, on the basis of whether or not the peak has been generated within a predetermined period which includes the timing of the operation specified by the specifying means; and calculation means for calculating biological information on the basis of a biological signal obtained by the biosensor and determination results obtained by the noise occurrence determining means.

In the mobile device according to the present invention, if an operation is performed while a biological signal is being obtained from a hand holding the mobile device, on the basis of whether a peak of the biological signal has been generated within a predetermined period which includes an operation timing, a determination is made as to whether this peak is body motion noise. Then, biological information is calculated on the basis of determination results and the obtained biological signal. That is, by using an operation detection function of the mobile device, a determination can be made as to whether a peak of a biological signal is body motion noise. Accordingly, in the mobile device including a biosensor for obtaining biological signals, without separately providing a sensor specially used for detecting the occurrence of body motion caused by operating the mobile device, biological information can be stably monitored while the mobile device is being held with a hand and is used.

The mobile device according to the present invention preferably further include subject determining means for determining whether or not a hand used for operating the operation means is the same hand as that from which a biological signal is being obtained by the biosensor. If it is determined by the subject determining means that the hand used for operating the operation means is the same hand as that from which a biological signal is being obtained, the noise occurrence determining means, preferably, make a noise occurrence determination, and if it is determined by the subject determining means that the hand used for operating the operation means is not the same hand as that from which a biological signal is being obtained, the noise occurrence determining means, preferably, does not make a noise occurrence determination.

In the mobile device according to the present invention, it is determined whether or not a hand used for operating the operation means is the same hand as that from which a biological signal is being obtained (sensed) by the biosensor. If the same hand as that from which a biological signal is being sensed is used for operating the operation means, the possibility that that the hand will be moved during the operation and body motion noise will be output is high. Accordingly, in this case, a noise occurrence determination is made so that noise can be detected. On the other hand, if the hand used for operating the operation means is not the same hand as that from which a biological signal is being sensed, the possibility that that body motion noise will occur is low. Accordingly, in this case, a noise occurrence determination is not made. With this arrangement, if a real peak due to a change in the condition of a body is generated around the operation timing, the possibility that this peak will be incorrectly determined to be body motion noise can be eliminated.

In the mobile device according to the present invention, the specifying means preferably specify a timing at which the operation means is turned ON and/or a timing at which the operation means is turned OFF, and the noise occurrence determining means preferably determine whether or not a peak of a biological signal obtained by the biosensor is body motion noise, on the basis of whether or not the peak has been generated within a predetermined period starting from a time point before the operation means has been turned ON until when the operation means has been turned ON and/or within a predetermined period starting from when the operation means has been turned OFF until a time point after the operation means has been turned OFF.

Body motion noise is likely to occur during a period from when a finger starts to move to an operation position until when the finger performs an operation (ON) and a period from when a finger is released (OFF) from an operation position until when the finger returns to an original position. In this case, it is determined whether or not a peak of an obtained biological signal is body motion noise, on the basis of whether or not the peak has been generated within a predetermined period starting from a time point before the operation means has been turned ON until when the operation means has been turned ON and/or within a predetermined period starting from when the operation means has been turned OFF until a time point after the operation means has been turned OFF. Thus, it is possible to more effectively detect the occurrence of body motion noise caused by an operation performed on the mobile device.

In the mobile device according to the present invention, the operation means preferably be a touch panel that detects a touch operation; the specifying means preferably specify a timing at which a finger touches the touch panel, and/or a timing at which a finger is released from the touch panel; and the noise occurrence determining means preferably determine whether or not a peak of a biological signal obtained by the biosensor is body motion noise, on the basis of whether or not the peak has been generated within a predetermined period starting from a time point before the finger has touched the touch panel until when the finger has touched the touch panel and/or within a predetermined period starting from when the finger has been released from the touch panel until a time point after the finger has been released from the touch panel.

As discussed above, body motion noise is likely to occur during a period from when a finger starts to move to a touch position until when the finger operates (touches) the touch position and a period from when a finger is released from a touch position until when the finger returns to an original position. In this case, it is determined whether or not a peak of an obtained biological signal is body motion noise, on the basis of whether or not the peak has been generated within a predetermined period starting from a time point before the finger has touched the touch panel until when the finger has touched the touch panel and/or within a predetermined period starting from when the finger has been released from the touch panel until a time point after the finger has been released from the touch panel. Thus, it is possible to more effectively detect the occurrence of body motion noise caused by a touch operation performed on the mobile device.

The mobile device according to the present invention preferably further include: display means for displaying a switch image, the display means and the touch panel being superposed on each other; calculation means for calculating, concerning a switch image displayed by the display means, a ratio of the number of times a touch operation has been determined to be body motion noise to the number of times a touch operation has been performed; and changing means for changing a position of the switch image to be displayed, on the basis of the ratio calculated by the calculation means.

In this case, the ratio of the number of times a touch operation has been determined to be body motion noise to the number of times a touch operation has been performed is calculated, and the position of a switch image is changed in accordance with the calculated ratio. Accordingly, concerning, for example, a switch image having a relatively high ratio of body motion noise, the display position of such a switch image can be changed. Thus, it is possible to move a switch image to a position at which body motion noise is unlikely to occur even if a touch operation is performed.

In the mobile device according to the present invention: the biosensor is preferably a sensor that obtains a biological signal having periodic peaks; and the predetermined period is preferably set on the basis of a peak interval of a biological signal obtained by the biosensor.

In this case, the predetermined period used for making a noise occurrence determination is set by considering a peak interval of an obtained biological signal. It is thus possible to appropriately perform a noise occurrence determination without interfering with sampling (obtaining) of biological signals.

According to the present invention, in a mobile device including a biosensor for obtaining biological signals, biological information can be obtained stably while the mobile device is being held with a hand and is used, without providing a sensor specially used for detecting body motion generated by operating the mobile device.

DETAILED DESCRIPTION OF THE PREFERRED EMBODIMENTS

Figure 1:
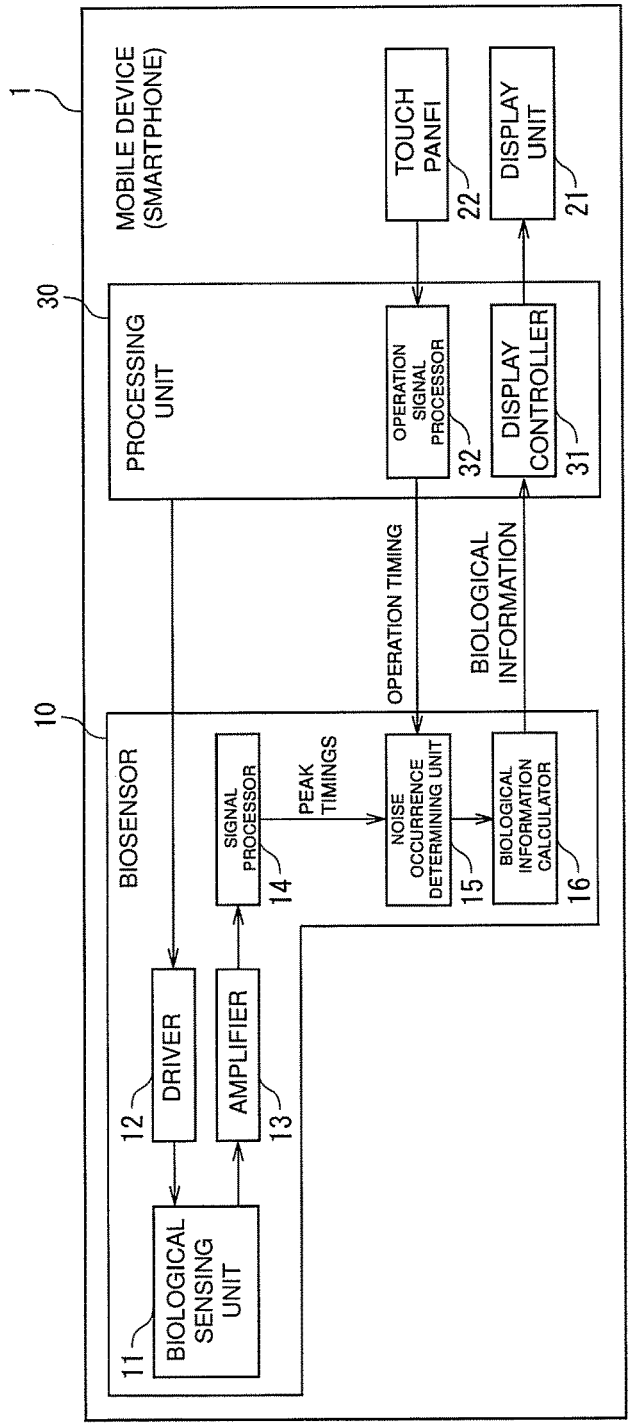
FIG. 1 is a block diagram illustrating the configuration of a mobile device according to a first embodiment.

Hereinafter, preferred embodiments of the present invention will be described below in detail with reference to the drawings. In the drawings, the same elements are designated by like reference numerals, and an explanation of the same element will be given only once.

First Embodiment

Figure 2:
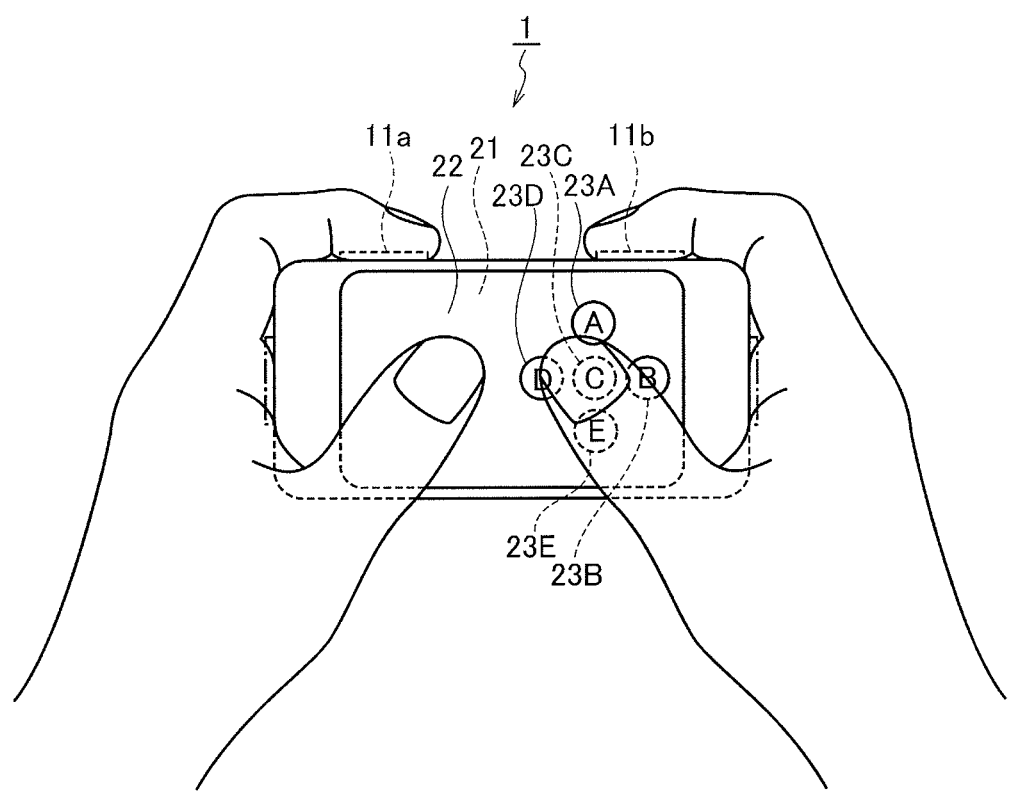
FIG. 2 illustrates an example of the state in which the mobile device according to the first embodiment is being used.

The configuration of a mobile device 1 according to a first embodiment will first be discussed below with reference to FIGS. 1 and 2. FIG. 1 is a block diagram illustrating the configuration of the mobile device 1. FIG. 2 illustrates an example of the state in which the mobile device 1 is being used.

The mobile device 1 is an electronic device which is held with hands and is used (operated), for example, a cellular phone, a smartphone, a mobile PC, such as a tablet PC, a mobile device, such as a mobile game machine, or a controller or a remote controller of a game machine. In particular, the mobile device 1 is an electronic device which allows a user to hold it with the hands and to operate switches of the device by using, for example, a finger. In this embodiment, the mobile device 1 will be described through illustration of a smartphone (hereinafter a mobile device may also be referred to as a "smartphone").

The smartphone 1 includes a biosensor 10 and has a function of monitoring a biological signal of a user while the user is operating the smartphone 1 by holding it with the hands. As operations using the smartphone 1, various operations, such as web browsing, inputting/selecting of telephone numbers, and writing email, are performed. Additionally, the smartphone 1 has a function of detecting and removing body motion noise which occurs from an operation while a biological signal is being monitored.

The smartphone 1 has a thin and generally rectangular parallelepiped shape, and a sheet-like display unit 21 and a touch panel 22 are superposed on each other and fixed to the front surface of the smartphone 1. The display unit 21 displays various information and operation screens. The display unit 21 serves as display means recited in the claims. The display unit 21 is constituted by, for example, a liquid crystal display (LCD). On the operation screen, switch images representing various switches are displayed. In the example shown in FIG. 2, five circular switch images 23A, 23B, 23C, 23D, and 23E are shown.

The touch panel 22 detects a touch operation performed by a hand. The touch panel 22 serves as operation means recited in the claims. An electrostatic capacitive method or a resistive film method, for example, may be used for detecting a touch operation. As a touch operation, the touch panel 22 is able to detect that a hand has touched the touch panel 22 or that a hand has been released from touch panel 22. Virtual two-dimensional coordinates are set on the surface of the touch panel 22, and when a user performs a touch operation, the touch panel 22 detects a position on the two-dimensional coordinates at which the user has touched, and outputs the detected touch position.

The smartphone 1 includes a processing unit 30 connected to the display unit 21 and the touch panel 22. The processing unit 30 is constituted by a microprocessor, a ROM, a RAM, a backup RAM, and so on. The processing unit 30 functions as a display controller 31 and an operation signal processor 32 as a result of the microprocessor executing a program stored in the ROM. The display controller 31 controls information displayed on the display unit 21.

The operation signal processor 32 processes an operation signal output from the touch panel 22 and specifies the content of an operation. More specifically, the operation signal processor 32 obtains coordinate information indicating a touch position from an operation signal and specifies the content of the operation on the basis of the touch position and the display positions of the switch images 23A through 23E.

The operation signal processor 32 also specifies a timing at which the operation detected by the touch panel 22 has been performed, on the basis of the operation signal. More specifically, as the operation timing, a timing at which a hand (finger) has touched the touch panel 22 or a timing at which a hand (finger) has been released from the touch panel 22 is specified. That is, the operation signal processor 32 serves as specifying means recited in the claims. The operation timing specified by the operation signal processor 32 is output to a noise occurrence determining unit 15, which will be discussed later.

The biosensor 10 is a sensor for obtaining biological signals from hands holding the smartphone 1. As the biosensor 10, for example, a photoplethysmographic sensor, an oxygen saturation sensor, a pulse pressure sensor, an electrocardiogram sensor, an electromyogram sensor, a skin resistance sensor, a sweat sensor, a skin temperature sensor, or a body fat sensor may be used. The smartphone 1 may include one biosensor or a plurality of biosensors. In this example, a description will be given, assuming that a photoplethysmographic sensor and an electrocardiogram sensor are used as the biosensor 10.

The biosensor 10 of this embodiment includes a biological sensing unit 11, a driver 12, an amplifier 13, a signal processor 14, a noise occurrence determining unit 15, and a biological information calculator 16. The biological sensing unit 11 is exposed to the surface of the smartphone 1, so that it can contact fingers or portions around the bases of fingers of palms when the smartphone 1 is held with hands. The biological sensing unit 11 is disposed, for example, on a lateral side, a region of a front side near a lateral side, or a region of a back side near a lateral side of the smartphone 1. The biological sensing unit 11 of this embodiment, as shown in FIG. 2, is constituted by a first sensing portion 11a and a second sensing portion 11b, which are disposed at both end portions of a top side of the smartphone 1, as indicated by the broken lines in FIG. 2. Alternatively, the first sensing portion 11a and the second sensing portion 11b may be disposed on a pair of shorter sides of the smartphone 1, as indicated by the long dashed dotted lines in FIG. 2.

The first sensing portion 11a includes a light emitting element, such as an LED or a VCSEL, and a light receiving element, such as a PD (photodiode). The light emitting element of the first sensing portion 11a is driven by the driver 12. The first sensing portion 11a serves as a photoplethysmographic sensor by monitoring absorption characteristics of hemoglobin within the blood flowing through a finger which is in contact with the first sensing portion 11a. The first sensing portion 11a includes an electrode, and this electrode forms a pair with an electrode of the second sensing portion 11b, thereby serving as an electrocardiogram sensor.

When a user holds the smartphone 1 with both hands, as in the state shown in FIG. 2, the index finger of a left hand contacts the electrode of the first sensing portion 11a, while the index finger of a right hand contacts the electrode of the second sensing portion 11b. When a sensing operation is started, a photoplethysmographic signal and an electrocardiogram signal are output from the sensing unit 11 (first and second sensing portions 11a and 11b). The output photoplethysmographic signal and electrocardiogram signal are amplified by the amplifier 13 and are subjected to A/D conversion. Then, the photoplethysmographic signal and the electrocardiogram signal are output to the signal processor 14. In this case, the photoplethysmographic signal and the electrocardiogram signal may be subjected to filtering processing so as to remove unwanted high or low frequency components.

The signal processor 14, the noise occurrence determining unit 15, and the biological information calculator 16 are constituted by a microprocessor, a ROM, a RAM, and so on. As a result of the microprocessor executing a program stored in the ROM, functions of the signal processor 14, the noise occurrence determining unit 15, and the biological information calculator 16 are implemented.

Figure 3:
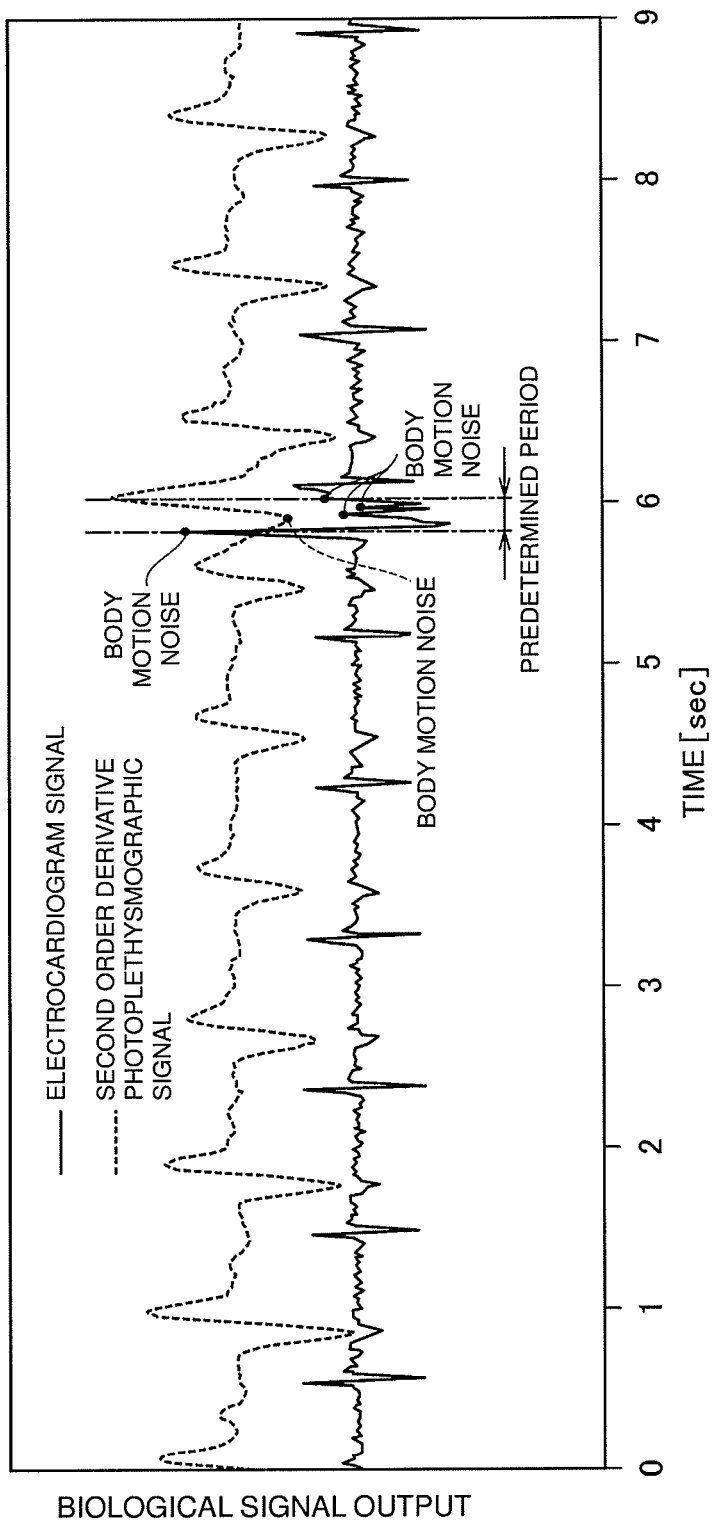
FIG. 3 illustrates an example of an electrocardiogram signal and an example of a second-order-derivative photoplethysmographic signal.

The signal processor 14 performs signal processing on the photoplethysmographic signal and the electrocardiogram signal. The signal processor 14 performs second order derivative on the photoplethysmographic signal so as to obtain a second-order-derivative photoplethysmographic signal (acceleration photoplethysmographic signal). Examples of the waveforms of the electrocardiogram signal and the second-order-derivative photoplethysmographic signal are shown in FIG. 3. In FIG. 3, the waveform indicated by the broken line is the waveform of the second-order-derivative photoplethysmographic signal, while the waveform indicated by the solid line is the waveform of the electrocardiogram signal.

In order to obtain biological information, concerning each of the second-order-derivative photoplethysmographic signal and the electrocardiogram signal, the signal processor 14 specifies timings at which peaks are generated (hereinafter referred to as "peak timings"). From the electrocardiogram signal, biological information concerning, for example, the heart rate, is obtained on the basis of the peak interval. From the second-order-derivative photoplethysmographic signal, biological information concerning, for example, the pulse rate, is obtained on the basis of the peak interval. The peak timings of the electrocardiogram signal and the second-order-derivative photoplethysmographic signal specified by the signal processor 14 are output to the noise occurrence determining unit 15.

The noise occurrence determining unit 15 compares each of the peak timings of a biological signal (including an electrocardiogram signal and a second-order-derivative photoplethysmographic signal) specified by the signal processor 14 with the operation timing input from the operation processor 30, and determines whether a peak of the biological signal has been generated within a predetermined period which includes the operation timing. Then, the noise occurrence determining unit 15 determines a peak of the biological signal generated within the predetermined period including the operation timing to be body motion noise caused by an operation.

The predetermined period including the operation timing may be a certain period starting from a time point before the operation timing until a time point after the operation timing. Alternatively, the predetermined period including the operation timing may be a certain period starting from a time point before the operation timing until the operation timing or a certain period starting from the operation timing until a time point after the operation timing. If the timing at which a finger touches the touch panel 22 is used as the operation timing, the period for which a relatively high level of body motion noise is likely to occur is a period from when the finger starts to move to a touch position until when the finger touches the touch position. Accordingly, in this case, a certain period starting from a time point before the operation timing until the operation timing is preferably used as the above-described predetermined period (determination period). On the other hand, if the timing at which a finger is released from the touch panel 22 is used as the operation timing, the period for which a relatively high level of body motion noise is likely to occur is a period from when the finger is released from the touch panel 22 until when the finger returns to an original position. Accordingly, in this case, a certain period starting from the operation timing until a time point after the operation timing is preferably used as the above-described predetermined period (determining period).

The length of the above-described predetermined period may be set as desired in accordance with the characteristics of a biological signal to be obtained. In the case of an electrocardiogram signal and a second order derivative photoplethysmographic signal, the predetermined period is preferably, for example, 0.1 seconds or shorter. Different lengths of the predetermined period may be set for the electrocardiogram signal and the second-order-derivative photoplethysmographic signal.

The biological information calculator 16 calculates biological information on the basis of the obtained biological signal and the noise determination results. The biological information calculator 16 removes peak signals determined to be body motion noise from the obtained electrocardiogram signal, and then calculates, for example, the heart rate. The biological information calculator 16 also removes peak signals determined to be body motion noise from the obtained second-order-derivative photoplethysmographic signal, and then calculates, for example, the pulse rate.

In the example shown in FIG. 3, concerning the second-order-derivative photoplethysmographic signal, one downward peak is contained within the predetermined period which includes the operation timing. The biological information calculator 16 disregards this downward peak contained within the predetermined period and calculates, for example, the pulse rate, on the basis of the intervals of downward peaks other than the disregarded peak. Concerning the electrocardiogram signal, four upward peaks are contained within the predetermined period which includes the operation timing. The biological information calculator 16 disregards these upward peaks contained within the predetermined period and calculates, for example, the heart rate, on the basis of the upward intervals of peaks other than the disregarded peaks. Biological information, such as, the heart rate and the pulse rate, is output to the display controller 31, and is displayed on the display unit 21. The biological information may be stored in the RAM.

Figure 4:
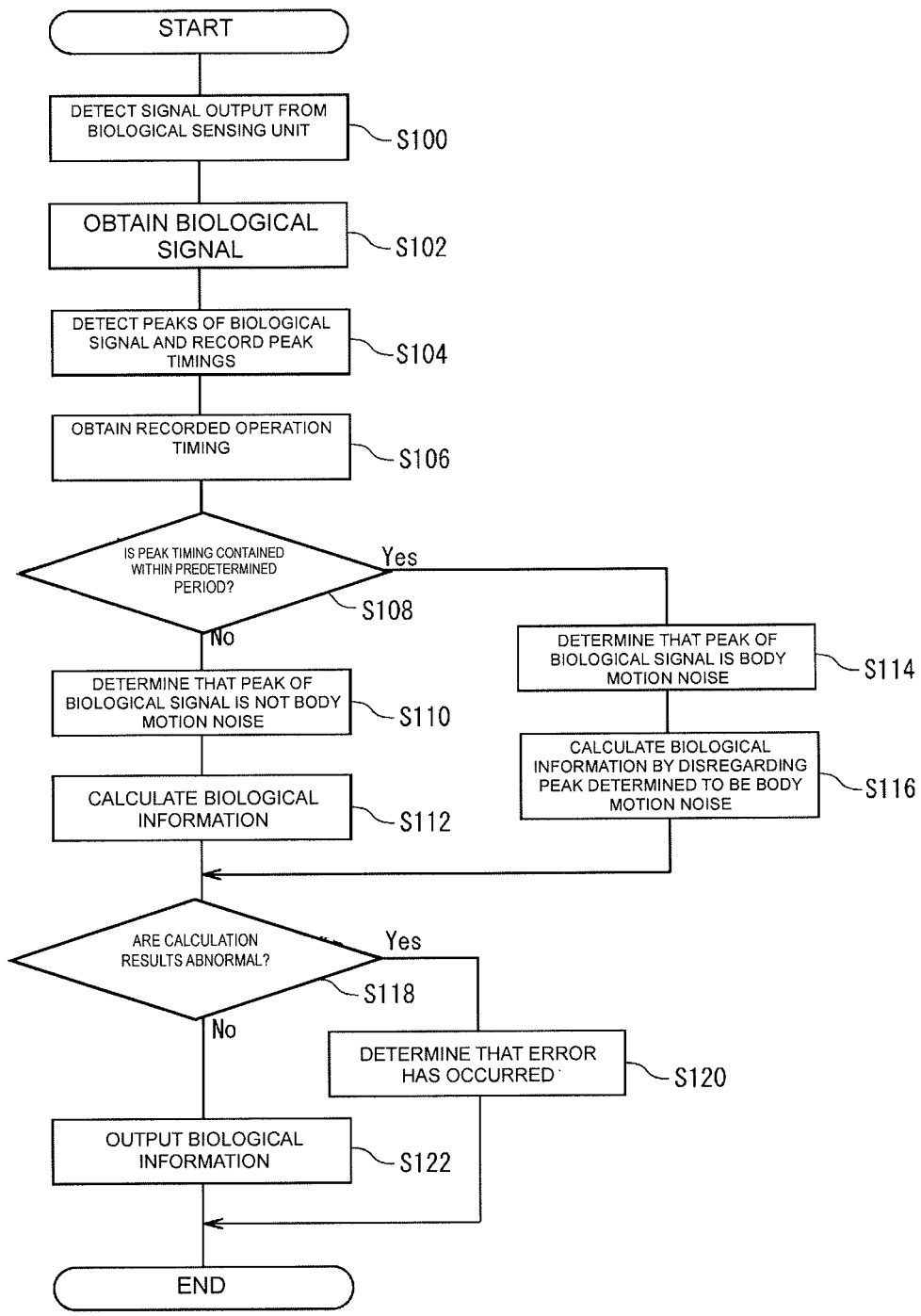
FIG. 4 is a flowchart illustrating a procedure of biological information generating processing performed by the mobile device according to the first embodiment.

An operation of the smartphone 1 will now be described below with reference to FIG. 4. FIG. 4 is a flowchart illustrating a procedure of generating processing for biological information performed by the smartphone 1. This processing is executed at a predetermined timing by the signal processor 14, the noise occurrence determining unit 15, and the biological information calculator 16.

In step S100, a signal output from the biological sensing unit 11 is detected. In step S102, the signal output from the biological sensing unit 11 is processed, so that a biological signal for calculating biological information can be obtained. In step S104, peaks of the biological signal are detected, and the peak timings are stored. Meanwhile, in the processing unit 30, if a touch operation has been detected, the operation timing of the touch operation has been obtained and stored. In step S106, the stored operation timing is read into the noise occurrence determining unit 15.

In step S108, each of the stored peak timings and the operation timing are compared with each other, and it is determined whether the peak timing is contained within a predetermined period which includes the operation timing. If it is determined that the peak timing is not contained within the predetermined period, the process proceeds to step S110. In step S110, it is determined that the peak of the biological signal is not body motion noise. Then, in step S112, biological information is calculated on the basis of peaks of the biological signal which have not been determined to be body motion noise. Then, the process proceeds to step S118.

On the other hand, if it is determined in step S108 that the peak timing is contained within the predetermined period which includes the operation timing, the process proceeds to step S114. In step S114, it is determined that the peak of the biological signal is body motion noise. Then, in step S116, biological information is calculated by disregarding the peak determined to be body motion noise. The process then proceeds to step S118.

In step S118, it is determined whether calculation results of biological information are abnormal. For example, if a peak interval of the biological signal is too short (for example, 0.1 seconds), it is determined that an abnormality has occurred. If it is determined in step S118 that the calculation results are abnormal, it is determined that an error has occurred (step S120). Then, data is discarded, and this processing is terminated. If it is determined in step S118 that calculation results are normal, in step S122, the biological information is output to the display unit 22 through the display controller 31 and is displayed. Thereafter, the processing is terminated.

As described above, according to this embodiment, if an operation is performed while a biological signal is being obtained from hands holding the smartphone 1, on the basis of whether a peak of the biological signal has been generated within a predetermined period which includes the operation timing, a determination is made as to whether this peak is body motion noise. Then, biological information is calculated on the basis of determination results and the obtained biological signal. That is, by using an operation detection function of the smartphone 1, a determination can be made as to whether a peak of a biological signal is body motion noise. Accordingly, in the smartphone 1 including a biosensor, without separately providing a sensor specially used for detecting body motion, biological information can be stably monitored while the smartphone 1 is being held with hands and is used.

As discussed above, body motion noise is likely to occur during a period from when a finger starts to move to a touch position until when the finger operates (touches) the touch position or during a period from when a finger is released from a touch position until when the finger returns to an original position. In this embodiment, it is determined whether or not noise has occurred, on the basis of whether a peak of an obtained biological signal has been generated during a predetermined period starting from a time point before a finger has touched the touch panel 22 until when the finger has touched the touch panel 22 and/or during a predetermined period starting from when a finger has been released from the touch panel 22 until a time point after the finger has been released from the touch panel 22. It is thus possible to more effectively detect body motion noise caused by a touch operation of the smartphone 1.

Modified Example of First Embodiment

Figure 5:
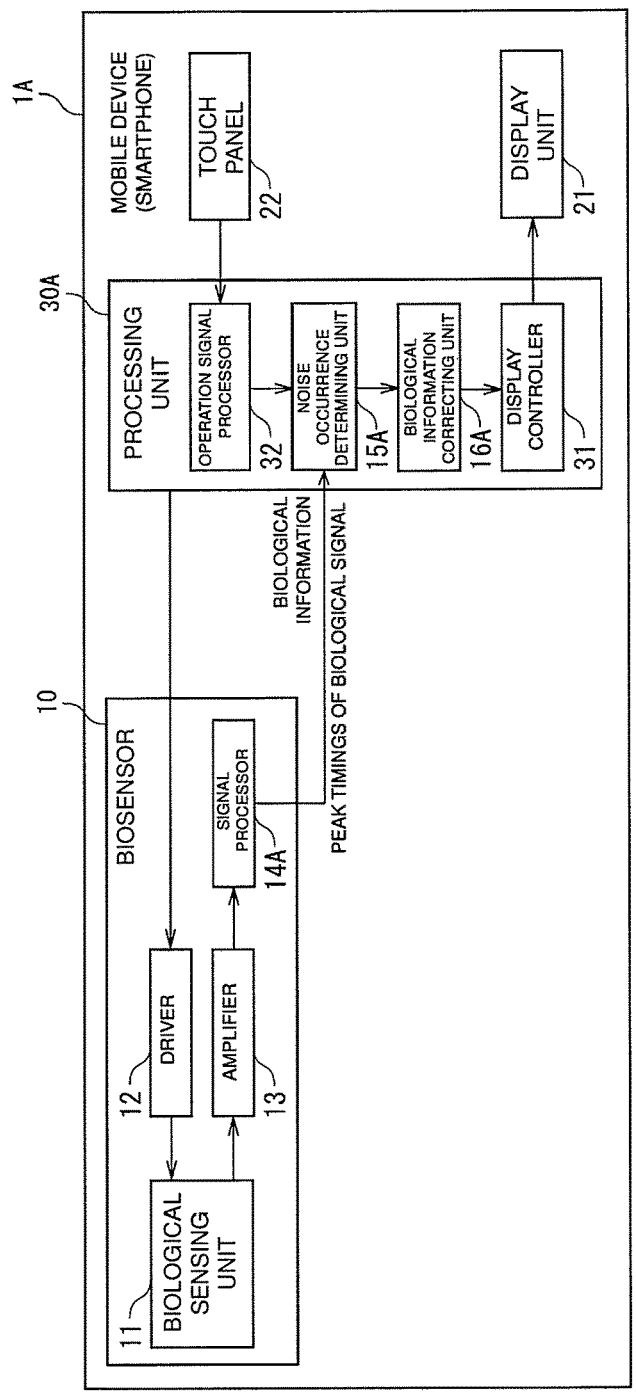
FIG. 5 is a block diagram illustrating the configuration of a mobile device according to a modified example of the first embodiment.

The configuration of a smartphone (mobile device) 1A according to a modified example of the first embodiment will now be described below with reference to FIG. 5. FIG. 5 is a block diagram illustrating the configuration of the smartphone 1A. Elements shown in FIG. 5 identical to or equivalent to the elements of the above-described smartphone 1 are designated by like reference numerals.

In the above-described smartphone 1, the noise occurrence determining unit 15 and the biological information calculator 16 are disposed in the biosensor 10. The smartphone 1A of this modified example is different from the smartphone 1 in that elements (a noise occurrence determining unit 15A and a biological information correcting unit 16A) corresponding to the noise occurrence determining unit 15 and the biological information calculator 16, respectively, are disposed in a processing unit 30A. The configurations of the other elements are identical to or equivalent to those of the above-described smartphone 1, and a detailed explanation thereof will thus be omitted.

The smartphone 1A includes a signal processor 14A instead of the above-described signal processor 14, a noise occurrence determining unit 15A instead of the noise occurrence determining unit 15, and a biological information correcting unit 16A instead of the biological information calculator 16. The biological information correcting unit 16A serves as calculation means recited in the claims.

The signal processor 14A specifies peak timings of a biological signal (including an electrocardiogram signal and a second-order-derivative photoplethysmographic signal), and then calculates biological information on the basis of the specified peak timings. The calculated biological information and the peak timings are output to the processing unit 30A. The noise occurrence determining unit 15A forming the processing unit 30A compares each of the peak timings output from the signal processing unit 14A with the operation timing specified by the operation signal processor 32, and then makes a determination as to whether noise has occurred. A determination as to the occurrence of noise is the same as that discussed above, and a detailed explanation thereof will thus be omitted. The biological information correcting unit 16A corrects the biological information output from the signal processor 14A if a peak of a biological signal is determined to be body motion noise.

Figure 6:
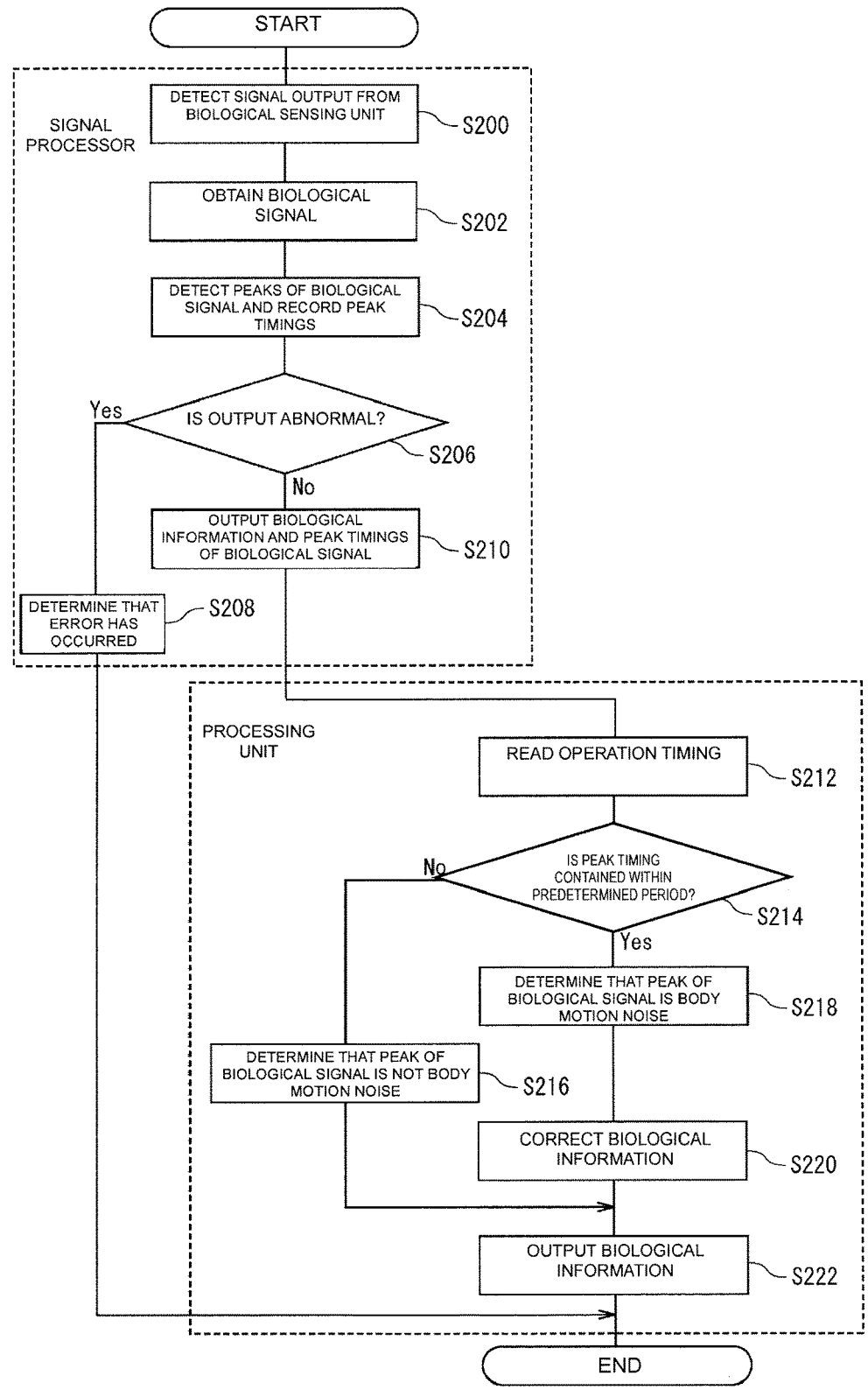
FIG. 6 is a flowchart illustrating a procedure of biological information generating processing performed by the mobile device according to the modified example of the first embodiment.

An operation of the smartphone 1A will now be described below with reference to FIG. 6. FIG. 6 is a flowchart illustrating a procedure of generating processing for biological information performed by the smartphone 1A. This processing is executed at a predetermined timing by the signal processor 14A and the processing unit 30A.

In step S200, a signal output from the biological sensing unit 11 is detected. In step S202, a biological signal for calculating biological information is obtained. In step S204, peaks of the biological signal are detected, and peak timings are stored. In step S206, it is determined whether the output is abnormal (for example, if the interval of the peak timings is abnormal). If it is determined in step S206 that the output is abnormal, it is determined that an error has occurred (step S208). Then, data is discarded, and this processing is terminated. If it is determined in step S206 that the output is normal, the process proceeds to step S210. In step S210, biological information is calculated on the basis of the peak timings, and the biological information and the peak timings are output from the signal processor 14A to the processing unit 30A.

Then, in step S212, the peak timings and the stored operation timing are read. Then, in step S214, each of the peak timings and the operation timing are compared with each other, and it is determined whether the peak timing is contained within a predetermined period which includes the operation timing. If it is determined that the peak timing is not contained within the predetermined period, the process proceeds to step S216. In step S216, it is determined that the peak of the biological signal is not body motion noise. Then, the process proceeds to step S222.

On the other hand, if it is determined in step S214 that the peak timing is contained within the predetermined period, the process proceeds to step S218. In step S218, it is determined that the peak of the biological signal is body motion noise. Then, in step S220, the biological information calculated by the signal processor 14A is corrected. That is, biological information is recalculated by disregarding the peak determined to be body motion noise. Then, in step S222, the biological information is output to the display unit 22 and is displayed through the display controller 31. Thereafter, the processing is terminated.

As described above, as in the above-described smartphone 1, in the smartphone 1A of this modified example, motion body can be detected without separately providing a sensor specially used for detecting body motion, thereby achieving stable monitoring of biological information. Although in this modified example a determination as to the abnormality of an output is made before a noise occurrence determination, it may be made after a noise occurrence determination. Additionally, although the signal processor 14A and the processing unit 30A are implemented by different microprocessors, functions of the signal processor 14A and the processing unit 30A may be implemented by a single microprocessor.

Second Embodiment

Figure 7:
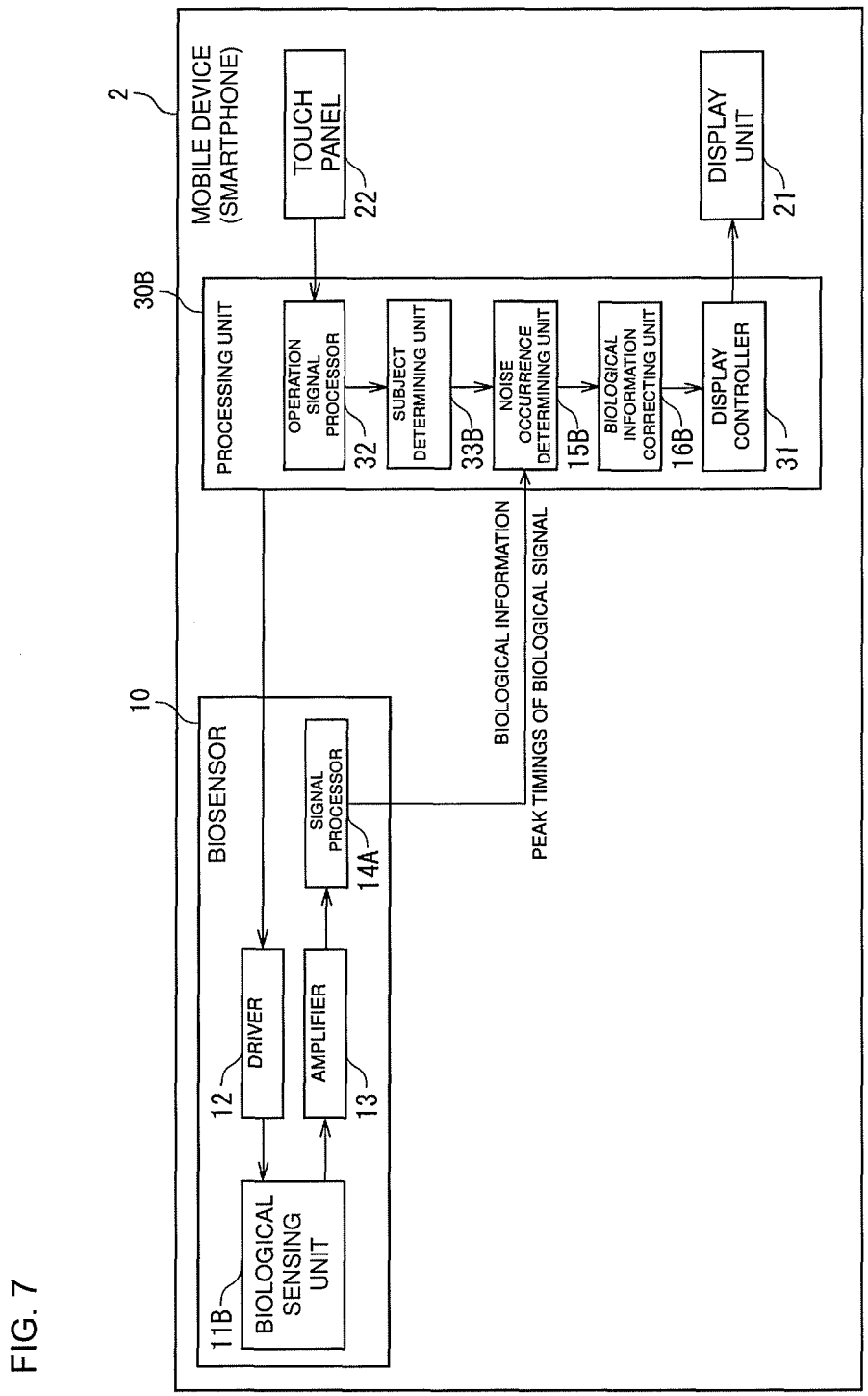
FIG. 7 is a block diagram illustrating the configuration of a mobile device according to a second embodiment.

The configuration of a smartphone (mobile device) 2 according to a second embodiment will now be described below with reference to FIG. 7. FIG. 7 is a block diagram illustrating the configuration of the smartphone 2. Elements shown in FIG. 7 identical to or equivalent to the elements of the modified example of the first embodiment are designated by like reference numerals.

In the above-described first embodiment, the right and left hands (fingers) holding the smartphone 1 are subjected to a sensing operation. Alternatively, a finger of only one hand may be subjected to a sensing operation. In this case, when a smartphone is operated by using a hand subjected to a sensing operation, the possibility that body motion noise will occur becomes high. However, when a smartphone is operated by using a hand which is not subjected to a sensing operation, body motion noise will not occur, or if it occurs, it is negligibly very small. Accordingly, in the smartphone 2 of the second embodiment, a determination is made as to whether a hand used for operating the smartphone 2 is the same hand as that subjected to a sensing operation, and if it is not the hand subjected to a sensing operation, a noise occurrence determination is not made.

The smartphone 2 of the second embodiment includes a biological sensing unit 11B instead of the biological sensing unit 11 of the smartphone 1A, and a noise occurrence determining unit 15B instead of the noise occurrence determining unit 15A of the smartphone 1A. The smartphone 2 also includes a biological information correcting unit 16B instead of the biological information correcting unit 16A. The smartphone 2 is different from the above-described smartphone 1A in that a processing unit 30B includes a subject determining unit 33B which determines whether a hand used for performing an operation is the same hand as that subjected to a sensing operation. The configurations of the other elements are identical to or similar to those of the smartphone 1A, and a detailed explanation thereof will thus be omitted.

The biological sensing unit 11B is a sensor, for example, a photoplethysmographic sensor, which performs a sensing operation when a hand contacts the sensor. The subject determining unit 33B determines whether a hand used for performing a touch operation is a hand from which a biological signal is being obtained (sensed) by using the biological sensing unit 11B. More specifically, the subject determining unit 33B determines whether a hand used for performing a touch operation is the same hand as that from which a biological signal is being obtained (sensed), on the basis of a mounting position of the biological sensing unit 11B and a display position of a switch image touched by a user. If, for example, the biological sensing unit 11B is disposed on the left side of the device and if a switch image displayed on the right side of the display unit 21 has been touched, the subject determining unit 33B determines that the hand used for performing a touch operation is not the same hand as that subjected to a sensing operation. If the biological sensing unit 11B is disposed on the left side of the device and if a switch image displayed on the left side of the display unit 21 has been touched, the subject determining unit 33B determines that the hand used for performing a touch operation is the same hand as that subjected to a sensing operation.

If it is determined that the hand used for performing a touch operation is the same hand as that subjected to a sensing operation, the noise occurrence determining unit 15B makes a noise occurrence determination. If it is determined that the hand used for performing a touch operation is not the same hand as that subjected to a sensing operation, the noise occurrence determining unit 15B does not make a noise occurrence determination. If a peak of a biological signal is determined to be body motion noise as a result of making a noise occurrence determination, the biological information correcting unit 16B corrects biological information output from the signal processor 14A. If a noise occurrence determination is not made, or if a peak of a biological signal is not determined to be body motion noise as a result of making a noise occurrence determination, the biological information correcting unit 16B does not correct the biological information.

Figure 8:
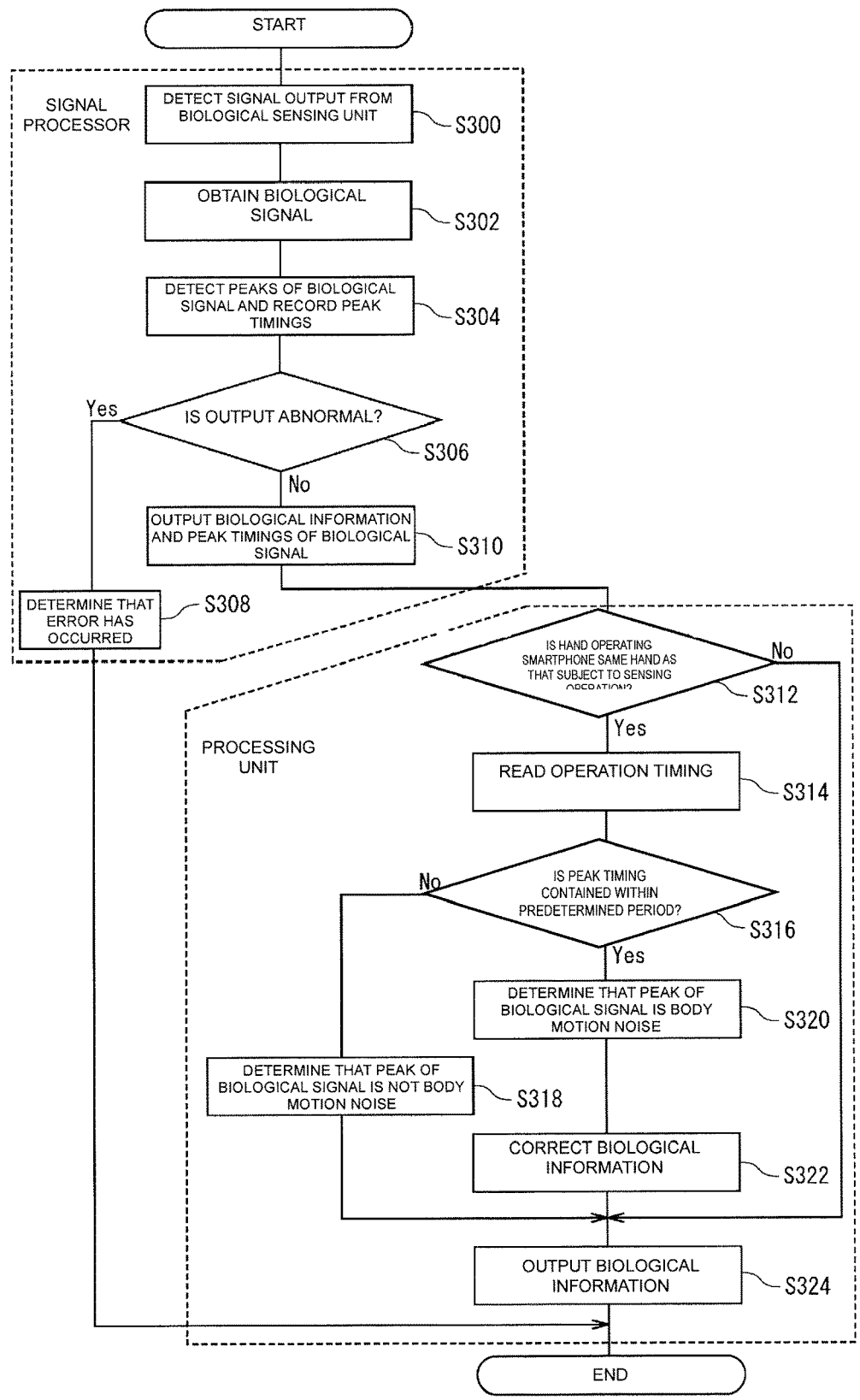
FIG. 8 is a flowchart illustrating a procedure of biological information generating processing performed by the mobile device according to the second embodiment.

An operation of the smartphone 2 will now be described below with reference to FIG. 8. FIG. 8 is a flowchart illustrating a procedure of generating processing for biological information performed by the smartphone 2. This processing is executed at a predetermined timing by the signal processor 14A and the processing unit 30B.

Steps S300 through S310 are similar to steps S200 through S210, respectively, and an explanation thereof will thus be omitted. After the biological information and the peak timings are output to the processing unit 30B in step 310, in step S312, it is determined whether a hand used for operating the smartphone 2 is the same hand as that subjected to a sensing operation. If the hand used for operating the smartphone 2 is not the same hand as that subjected to a sensing operation, the process proceeds to step S324. In step S324, biological information is output without making a noise occurrence determination. In contrast, if the hand used for operating the smartphone 2 is the same hand as that subjected to a sensing operation, the process proceeds to step S314. As in steps S212 through S222, in steps S314 through S324, respectively, a noise occurrence determination is made, and if a peak is determined to be body motion noise, biological information is corrected. In contrast, if a peak is not determined to be body motion noise, biological information is not corrected and is output as it is. The processing is then terminated.

As discussed above, in this embodiment, a noise occurrence determination is not made if a hand used for operating the smartphone 2 is not the same hand as that subjected to a sensing operation. Accordingly, if a real peak due to a change in the condition of a body is generated around the operation timing, the possibility that this peak will be incorrectly determined to be body motion noise can be eliminated.

Third Embodiment

Figure 9:
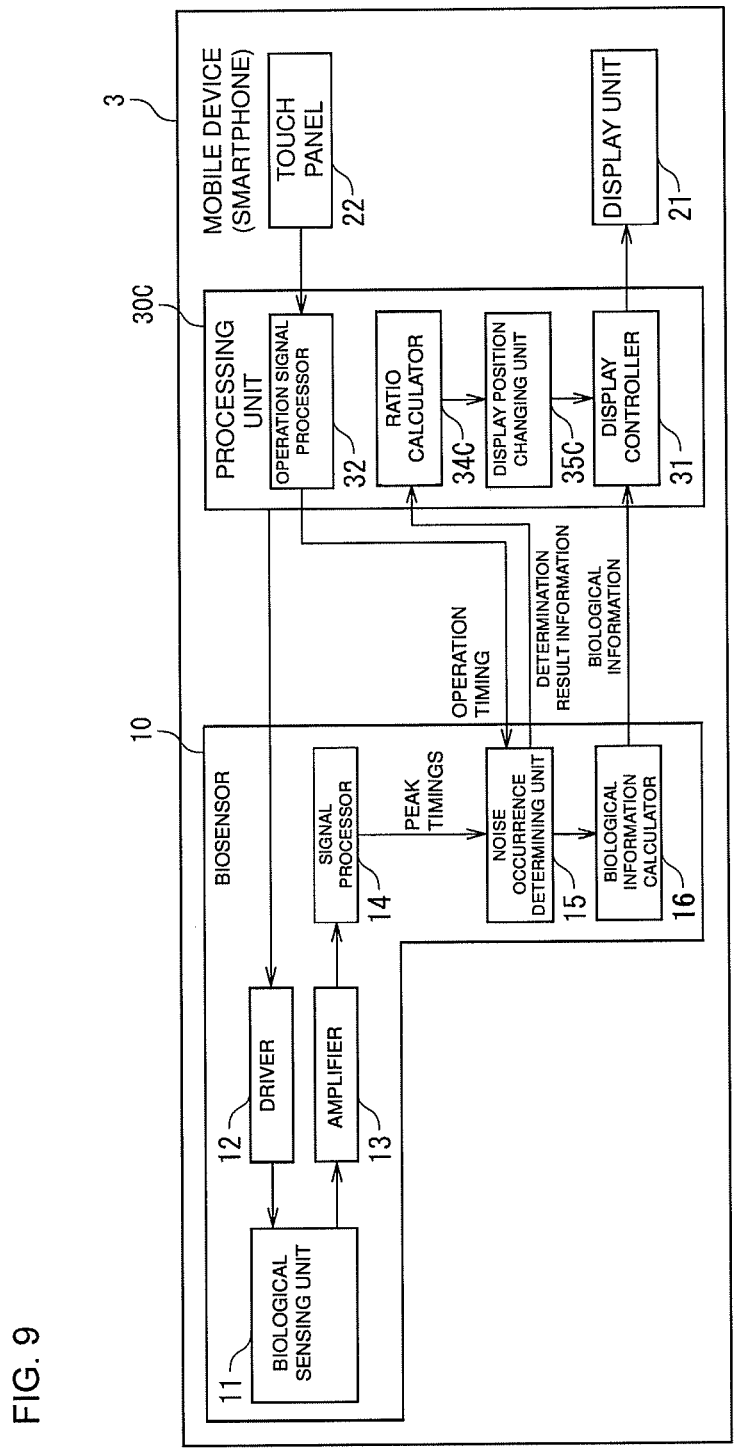
FIG. 9 is a block diagram illustrating the configuration of a mobile device according to a third embodiment.
Figure 10:
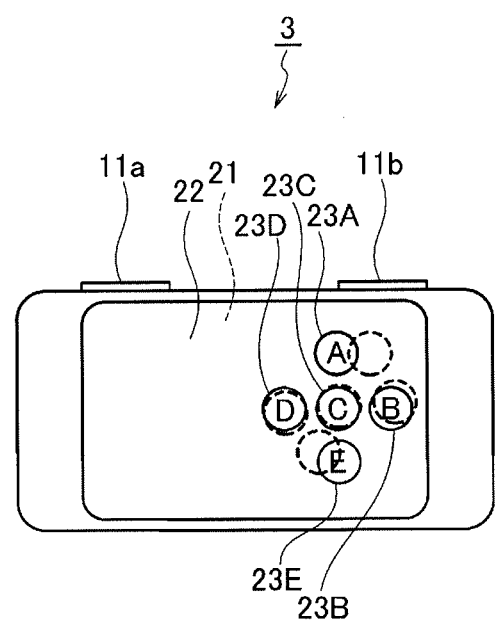
FIG. 10 is a view for explaining a method for changing positions of switch images displayed on the mobile device according to the third embodiment.

The configuration of a smartphone (mobile device) 3 according to a third embodiment will now be described below with reference to FIGS. 9 and 10. FIG. 9 is a block diagram illustrating the configuration of the smartphone 3. FIG. 10 is a view for explaining a method for changing positions of switch images displayed on a display unit 21 of the smartphone 3. Elements shown in FIG. 9 identical to or equivalent to the elements of the smartphone 1 of the first embodiment are designated by like reference numerals.

Concerning each of a plurality of switch images 23A through 23E, the smartphone 3 calculates the ratio of the number of times a touch operation is determined to be body motion noise to the number of times a touch operation is performed, and changes the display position of a switch image having a high ratio. Accordingly, a processing unit 30C of the smartphone 3 includes a ratio calculator 34C and a display position changing unit 35C in addition to the elements forming the processing unit 30 of the smartphone 1. The configurations of the other elements are identical to or similar to those of the smartphone 1, and a detailed explanation thereof will thus be omitted.

Concerning each of the plurality of switch images 23A through 23E, the ratio calculator 34C calculates the ratio of the number of times a touch operation is determined to be body motion noise to the number of times a touch operation is performed (hereinafter such a ratio will be referred to as a "determination ratio"). That is, the ratio calculator 34C serves as calculation means recited in the claims. More specifically, the ratio calculator 34C reads determination result information including the operation timing and determination results from the noise occurrence determining unit 15, and calculates the determination ratio by using the determination result information. For example, the ratio calculator 34C first stores the operation timing and the determination results in association with the display position of each of the switch images 23A through 23E. Then, the ratio calculator 34C calculates determination ratios every time operations have been performed for a certain period or a certain number of times.

In this case, it is presumable that a switch image having a relatively high determination ratio is located at a position at which motion body noise is likely to occur, and that a switch image having a relatively low determination ratio is located at a position at which motion body noise is unlikely to occur. Assuming that the determination ratios of the switch images 23A through 23E have been calculated as 60%, 20%, 10%, 30%, and 70%, respectively, switch images located at positions at which motion body noise is likely to occur are supposed to be the switches images 23A and 23E and switch images located at positions at which motion body noise is unlikely to occur are supposed to be the switches images 23B and 23C. The calculated determination ratios are output to the display position changing unit 35C.

The display position changing unit 35C changes the positions at which switch images are displayed on the display unit 21, on the basis of determination ratios. For example, among the five switch images 23A through 23E, the display position changing unit 35C changes the display positions of the switch images 23A and 23E having relatively high determination ratios so that they will be located closer to the display positions of the switch images 23B and 23C having relatively low determination ratios. With this arrangement, the display positions of the switch images can be corrected so that body motion noise will unlikely to occur. If a switch image having a relatively high determination ratio is located too close to a switch image having a relatively low determination ratio, it may be difficult for a user to perform an operation. In this case, it is preferable that the position of the switch image having a relatively low determination ratio is slightly displaced in an opposite direction. The circles indicated by the broken lines in FIG. 10 indicate corrected display positions of the switch images 23A through 23E as a result of performing the above-described correction processing several times.

Figure 11:
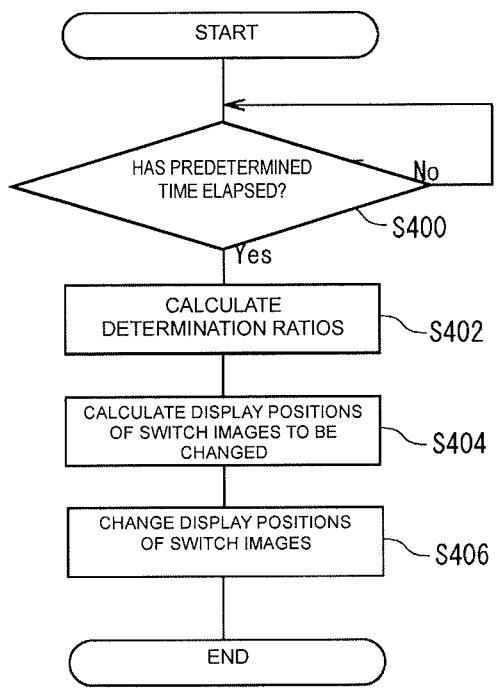
FIG. 11 is a flowchart illustrating a procedure of changing processing for display positions of switch images performed by the mobile device according to the third embodiment.

An operation of the smartphone 3 will now be described below with reference to FIG. 11. FIG. 11 is a flowchart illustrating a procedure of changing processing for display positions of switch images performed by the smartphone 3. This processing is executed at a predetermined timing by the processing unit 30C.

First, in step S400, it is determined whether a predetermined time has elapsed after previously performing changing processing for display positions. In step S400, instead of using the predetermined time, a determination may be made based on whether a touch operation has been performed a predetermined number of times after previously performing changing processing for display positions. If the predetermined time has not elapsed, step S400 is repeated until the predetermined time has elapsed. If the predetermined time has elapsed, the process proceeds to step S402.

In step S402, a determination ratio is calculated for each of the five switch images 23A through 23E. Then, in step S404, display positions of the switch images to be changed are calculated on the basis of the determination ratios calculated in step S402. Then, in step S406, the display positions of the switch images are changed.

As discussed above, according to this embodiment, since display positions of switch images are changed on the basis of determination ratios, they can be moved to positions at which body motion noise caused by a touch operation is unlikely to occur. Thus, switch images can be located at optimal positions according to the user (for example, according to the size of user's hands or the manner in which the user holds a smartphone).

While the present invention has been described with reference to the embodiments, it is to be understood that the invention is not limited to the disclosed embodiments and that various modifications may be made. For example, in the above-described embodiments, the touch panel 22 is used as operation means. Alternatively, hardware switches may be used.

Additionally, in the above-described embodiments, the operation timing is specified as to a touch operation (tap operation) on the touch panel 22. However, the operation timing is not restricted to a timing of a touch operation. For example, a timing at which a dragging operation while holding a finger on the touch panel 22 is detected may be specified as the operation timing. In this case, a peak of a biological signal generated within a predetermined period including a dragging operation may be determined to be body motion noise.

REFERENCE SIGNS LIST 1, 1A, 2, 3 smartphone
10, 10C biosensor
11 biological sensing unit
14, 14A signal processor
15, 15A, 15B noise occurrence determining unit
16 biological information calculator
16A biological information correcting unit
21 display unit
22 touch panel
32 operation signal processor
33B subject determining unit
34C ratio calculator
35C display position changing unit

The invention claimed is:
1. A mobile device comprising:
a housing which can be held by one or both hands of a user;
a biosensor coupled to the housing and configured to generate an electric signal indicative of a biological function of the user when at least one finger of one or both of the hands of the user are placed in an operative relationship with the biosensor, the electrical signal including electrical noise caused by certain body motions of the user;
an input sensor coupled to the housing and configured to allow a user to perform an input operation using at least one finger of one or both of the hands of the user while at least one finger of one or both hands of the user are in the operative relationship with the biosensor; and
a processor configured to calculate biological information indicative of the biological function of the user as a function of the electrical signal and in a manner that corrects for the electrical noise caused by the body motion of the user, the processor being further configured to specify at least one of a timing when a finger touches the input sensor and a timing when the finger is released from the input sensor, the processor calculating the biological information by:
determining a timing when the input operation occurred;
determining a time period which overlaps the timing when the input operation occurred, the time period is one of a first time period starting from a time point before the finger touches the input sensor until a time point when the finger touches the input sensor and a second time period starting a time point when the finger has been released from the input sensor until a time point after the finger has been released from the input sensor;
determining whether a peak of the electrical signal generated by the biosensor is electrical noise created by the body motion of the user based on whether the peak of the electrical signal is generated within the time period; and
calculating the biological information based on the electrical signal generated by the biosensor and the determination of whether the peak of the electrical signal is electric noise created by the body motion of the user.

2. The mobile device according to claim 1, wherein the processor is further configured to determine whether the at least one finger that performs the input operation and the at least one finger that is in operative contact with the biosensor are part of the same hand.

3. The mobile device according to claim 2, wherein, if the processor determines that the at least one finger that performs the input operation and the at least one finger that is in operative contact with the biosensor are part of the same hand, the processor determines that the peak of the biological signal is electric noise caused by body motion of the user.

4. The mobile device according to claim 2, wherein, if the processor determines that the at least one finger that performs the input operation and the at least one finger that is in operative contact with the biosensor are not part of the same hand, the processor determines that the peak of the biological signal is not electric noise caused by body motion of the user.

5. The mobile device according to claim 1, wherein the processor is further configured to specify when the input operation begins and when the operation ends.

6. The mobile device according to claim 5, wherein the time period is one of a first time period that starts at a time point before the input operation begins and stops when the input operation begins and a second time period that starts when the input operation ends and stops at a later time point after the input operation ends.

7. The mobile device according to claim 1, wherein the input sensor is a touch panel configured to detect a touch operation.

8. The mobile device according to claim 7, further comprising a display configured to display a switch image, the display and the touch panel being superposed on each other, and wherein the processor is further configured to:
calculate, with respect to the switch image displayed by the display, a ratio of the number of times a touch operation has been determined to include electrical noise caused by body motion of the user to the number of times a touch operation has been performed, and
change a position of the switch image on the basis of the calculated ratio.

9. The mobile device according to claim 1, wherein the electric signal has periodic peaks and the time period is set on the basis of a peak interval of the electric signal.

10. The mobile device according to claim 1, wherein the operative relationship is at least one finger of one or both of the hands of the user being in physical contact with the biosensor.

11. The mobile device according to claim 1, wherein the input sensor is not an acceleration sensor.

12. The mobile device according to claim 1, wherein the input sensor is a touch sensor.

13. The mobile device according to claim 1, wherein the biosensor and the input sensor are located on different sides of the housing.

14. A method of calculating biological information from a user of a mobile device, the method comprising:

detecting, using a biosensor coupled to a housing of the mobile device, a biological function of the user and generating an electric signal indicative of the biological function when at least one finger of one or both of the hands of the user are placed in an operative relationship with the biosensor, the electrical signal including electrical noise caused by certain body motions of the user;

an input sensor coupled to the housing and configured to allow a user to perform an input operation using at least one finger of one or both of the hands of the user while at least one finger of one or both hands of the user are in the operative relationship with the biosensor;

receiving an input operation on an input sensor from at least one finger of one or both of the hands of the user while at least one finger of one or both hands of the user are in the operative relationship with the biosensor; and using a processor to calculate biological information indicative of the biological function of the user as a function of the electrical signal and in a manner that corrects for the electrical noise caused by the body motion of the user, the processor also specifying at least one of a timing when a finger touches the input sensor and a timing when the finger is released from the input sensor, the processor calculating the biological information by:

determining a timing when the input operation occurred;

determining a time period which overlaps the timing when the input operation occurred, the time period being one of a first time period starting from a time point before the finger touches the input sensor until a time point when the finger touches the input sensor and a second time period starting at a time point when the finger has been released from the input sensor until a time point after the finger has been released from the input sensor;

determining whether a peak of the electrical signal generated by the biosensor is electrical noise created by the body motion of the user based on whether the peak of the electrical signal is generated within the time period; and calculating the biological information based on the electrical signal generated by the biosensor and the determination of whether the peak of the electrical signal is electric noise created by the body motion of the user.

15. The method according to claim 14, wherein the electric signal has periodic peaks and the time period is set on the basis of a peak interval of the electric signal.

16. The method according to claim 14, wherein the operative relationship is at least one finger of one or both of the hands of the user being in physical contact with the biosensor.

17. The method according to claim 14, wherein the input sensor is not an acceleration sensor.

18. The method according to claim 14, wherein the biosensor and the input sensor are located on different sides of the housing.

19. The method according to claim 14, wherein the input sensor is a touch sensor.

* * * * *